United States Patent [19]

Teulon

[11] 4,156,000
[45] May 22, 1979

[54] CYCLOPENTA[B]THIOPHENE DERIVATIVES

[75] Inventor: Jean-Marie Teulon, La Celle Saint Cloud, France

[73] Assignee: Hexachimie, Rueil Malmaison, France

[21] Appl. No.: 929,740

[22] Filed: Jul. 31, 1978

Related U.S. Application Data

[62] Division of Ser. No. 775,534, Mar. 8, 1977, Pat. No. 4,122,091.

[30] Foreign Application Priority Data

Mar. 12, 1976 [GB] United Kingdom ............... 10049/76

[51] Int. Cl.² ................. C07D 413/12; A61K 31/535
[52] U.S. Cl. ................................ 424/248.51; 544/146
[58] Field of Search .................... 544/146; 424/248.51

[56] References Cited

U.S. PATENT DOCUMENTS 3,865,842  2/1975  Robba et al. ........................ 544/146

Primary Examiner—Natalie Trousof
Assistant Examiner—R. W. Ramsuer
Attorney, Agent, or Firm—Fulwider, Patton, Rieber, Lee & Utecht

[57] ABSTRACT

Cyclopenta[b]thiophene derivatives of formula:

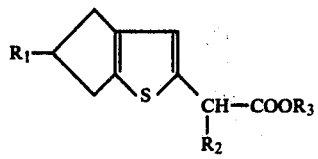

in which $R_1$ is lower alkyl, $R_2$ is hydrogen or lower alkyl, and $R_3$ is hydrogen, lower alkyl, or aminoalkyl, and their salts are useful in therapy particularly as analgesic and anti-inflammatory agents.

9 Claims, No Drawings

CYCLOPENTA[B]THIOPHENE DERIVATIVES

REFERENCE TO RELATED APPLICATIONS

This application is a divisional application of my parent application, Ser. No. 775,534, filed on Mar. 8, 1977 now U.S. Pat. No. 4,122,091 and claiming benefit of prior British specification No. 10049 filed on Mar. 12, 1976. The subject matter of this application is directed to esters of the above formula wherein $R_3$ represents a heterocyclo-alkyl group, such as a morpholinoethyl ester.

The present invention provides new cyclopenta[b]thiophene derivatives of the general formula:

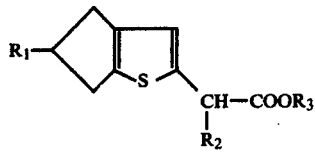
(I)

in which $R_1$ represents a straight or branched-chain alkyl radical of 1 to 4 carbon atoms, preferably ethyl or isopropyl, $R_2$ represents a hydrogen atom or an alkyl radical of 1 to 4 carbon atoms, especially methyl, and $R_3$ represents a hydrogen atom, an alkyl radical of 1 to 4 carbon atoms, preferably ethyl, or an aminoalkyl group of formula:

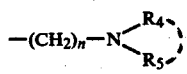

where n is 2 or 3, preferably 2, and $R_4$ and $R_5$ taken separately each denote alkyl of 1 to 4 carbon atoms, preferably methyl, or cycloalkyl, preferably cyclopentyl or cyclohexyl, or $R_4$ and $R_5$ taken together can form, with the nitrogen atom to which they are attached, a heterocyclic structure of 5 to 7 ring members preferably a saturated mononuclear heterocyclic ring containing carbon and nitrogen and optionally not more than one additional heteroatom which is oxygen, sulphur or nitrogen, for example, morpholino, and the pharmaceutically acceptable inorganic salts of the derivatives of formula I in which $R_3=H$, e.g. the sodium, potassium, calcium, aluminium and copper salts, and the acid addition salts, e.g. the hydrochloride, oxalate, malonate, or succinate, of the derivatives of formula I in which $R_3$ is an aminoalkyl radical.

The compounds of formula I possess valuable pharmacological activity and can be used in therapy, especially as analgesic and anti-inflammatory agents.

According to the invention, the compounds of the formula I in which $R_3$ is H are prepared either (1) by alkaline or acid hydrolysis of a nitrile of the formula:

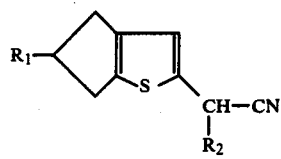
(II)

or (2) by alkaline hydrolysis of an ester of the formula I in which $R_3$ is alkyl of 1 to 4 carbon atoms, or (3) by decarboxylation of a malonic acid of the formula:

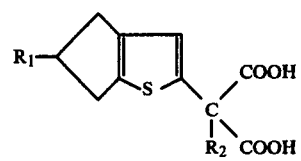
(III)

The alkaline hydrolysis of the nitriles of the formula II can be effected with an alkali metal hydroxide in an aqueous alcoholic medium, preferably at the reflux temperature of the solvent. The cooled reaction mixture is dissolved in a mixture of ice and water, the solution is rendered slightly acid, for example by adding hydrochloric acid, and the desired compound is extracted with a suitable solvent, for example diethyl ether. The evaporation of the ether extract gives the desired compound, which can be recrystallised from an appropriate solvent, for example petroleum ether.

The acid hydrolysis of the nitriles of the formula II can advantageously be effected with a mixture of acetic acid and aqueous sulphuric acid or with a mixture of acetic acid and aqueous hydrochloric acid, at the reflux temperature of the solvent.

The decarboxylation of the malonic acids of the formula III can be effected by heating to above the melting point of the said malonic acids, preferably in a vacuum.

The compounds of formula I in which $R_3$ is alkyl of 1 to 4 carbon atoms can be prepared by esterification of the corresponding acid of the formula I in which $R_3$ is hydrogen, with an alkanol of formula $R_3$—OH, preferably in the presence of a trace of concentrated sulphuric acid or hydrogen chloride gas.

The compounds of the formula I in which $R_3$ is an aminoalkyl group can be prepared either (A) by reaction of a chloride of the corresponding acid of the formula I in which $R_3$ is H, with an aminoalcohol of the formula:

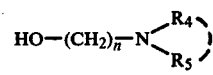

or (B) by reaction of a metal salt of the corresponding acid of the formula I in which $R_3$ is H, with a halogen derivative of an alkylamine of the formula:

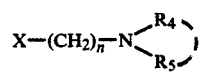

wherein X is a halogen atom, especially chlorine, in accordance with the following reaction scheme:

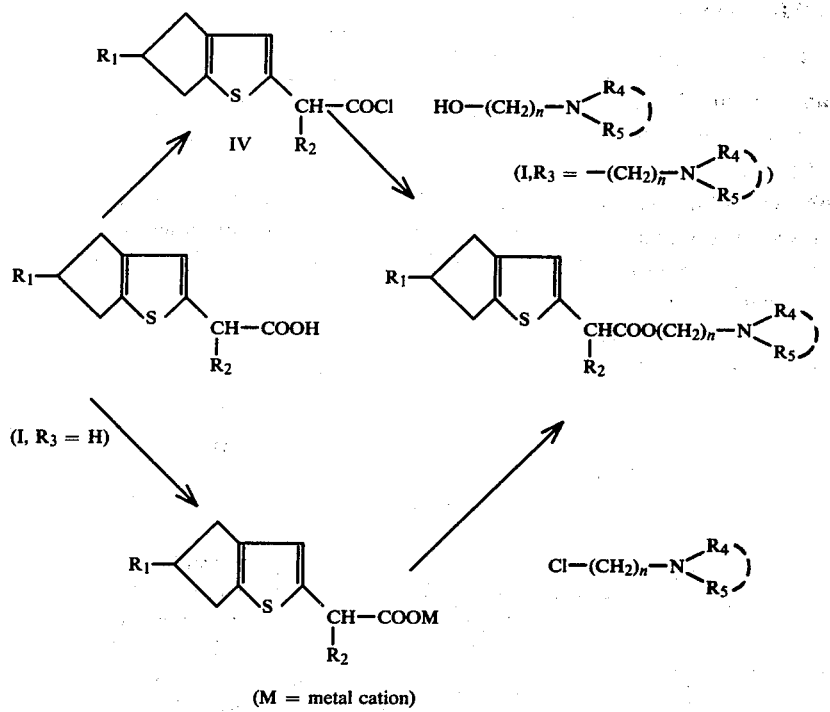

(M = metal cation)

The acid of the formula I, in which $R_3$ is H, is converted into its acid chloride by the action of thionyl chloride or phosphorus pentachloride on the said acid in an aromatic hydrocarbon medium, at the reflux temperature of the solvent.

The reaction of the acid chloride with an aminoalcohol of the formula:

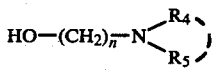

can be effected in an aromatic hydrocarbon solvent such as benzene or toluene, in the presence of a base, especially triethylamine, as an acceptor for the hydrochloric acid formed during the reaction.

To prepare the starting nitriles of the formula II, a 4,5-dihydro-6H-cyclopenta[b]thiophene compound of formula (VII) below is first prepared by reduction of the corresponding 6-oxo derivative by a Clemmensen reaction or by a catalytic hydrogenation under pressure. The 4,5-dihydro-6-oxo-6H-cyclopenta[b]thiophene derivatives of formula (VI) are in turn obtained by cyclising 1-(thienyl-2')-propan-3-ol-1-ones substituted in the 2-position of formula (V), using a strong acid such as sulphuric acid or polyphosphoric acid. The compounds of formula V are synthesised by an addition reaction of formaldehyde (or trioxymethylene) with a thienone in a basic medium, in a polar solvent, such as dimethylsulphoxide, hexamethylphosphotriamide dimethylformamide, or N-methyl-pyrrolidone. The reaction scheme is as follows:

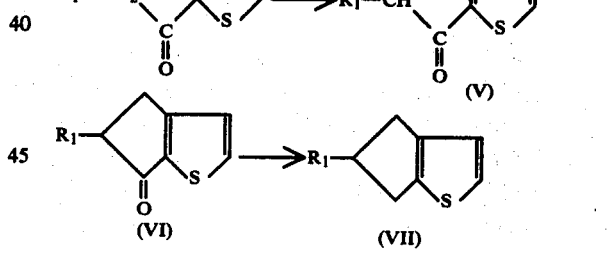

A nitrile group may be introduced into a 4,5-dihydro-6H-cyclopenta[b]thiophene compound of formula (VII) via the corresponding aldehyde of formula (VIII) obtained by a Vilsmeier reaction using phosphorus oxychloride and N-methylformanilide, this aldehyde being reacted with rhodamine in the presence of sodium acetate in an acetic acid medium under reflux, to form the 5'-(cyclopenta[b]-thienylidene-2)-4'-oxo-2'-thioxo-thiazolidine of formula (IX) below, which is heated in a basic medium, for example aqueous sodium hydroxide solution, to break the thiazolidine ring. The solution is rendered slightly acid to precipitate 3'-(cyclopenta[b]-thienyl-2)-2-thioxo-propionic acid (X), which is treated with hydroxylamine in ethanol to form the 3'-(cyclopenta[b]thienyl-2-2'-oximino-propionic acid derivative of formula (XI) below, which is reacted with acetic anhydride to give the (cyclopenta[b]thienyl-2)-acetonitrile derivative of formula (II). These reactions may be represented by the following scheme:

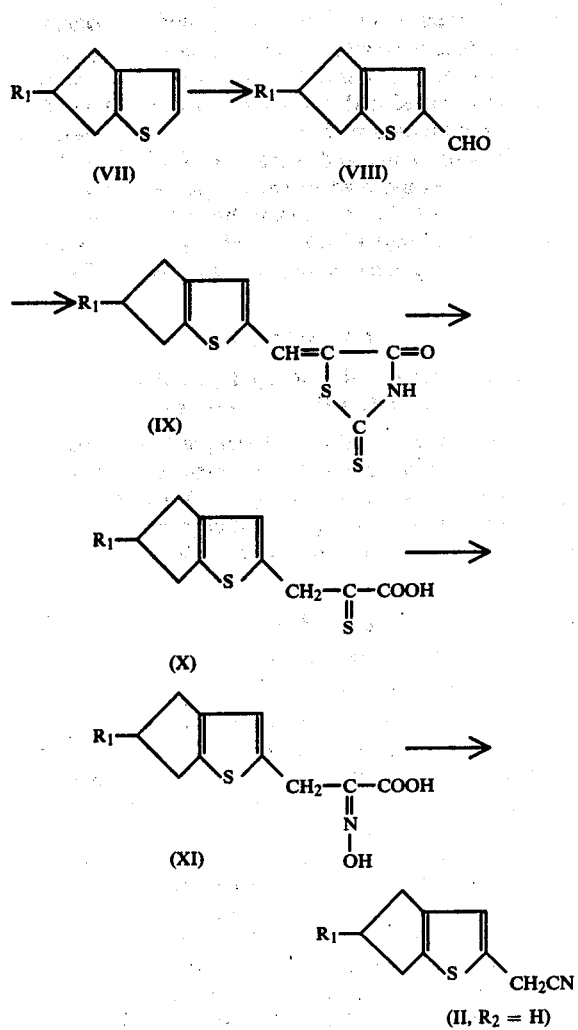

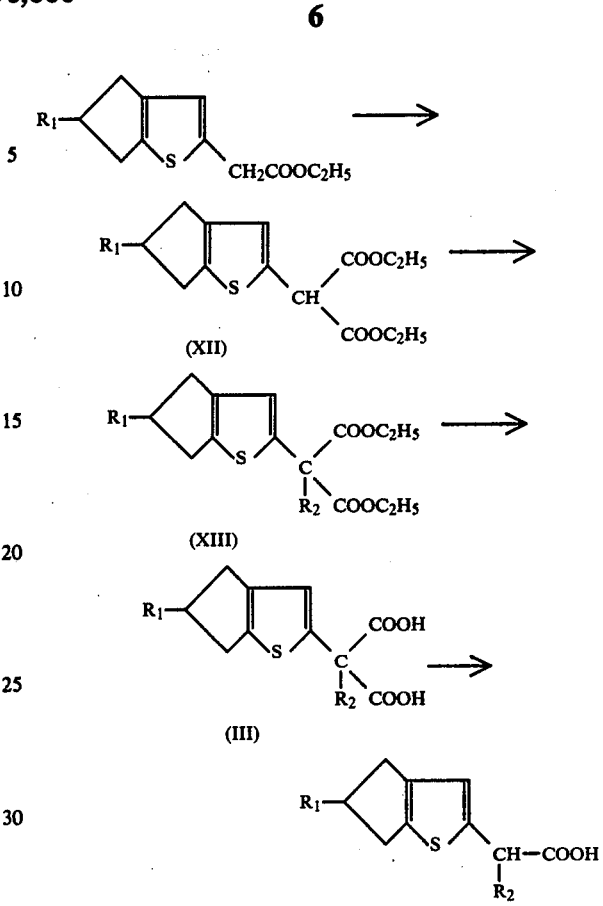

A lower alkyl radical, especially a methyl radical, can be introduced into the α-position of the nitrile (of the formula II, $R_2$=H) by the action of a metallising agent such as sodium hydride, potassium hydride, sodium amide, potassium amide and potassium tertiary-butylate, followed by the reaction of this metallised derivative with methyl iodide as follows:

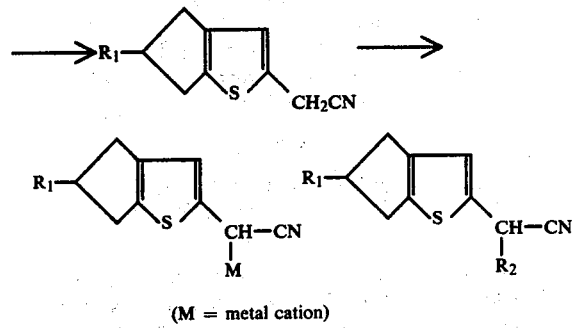

(M = metal cation)

Furthermore, the α-substituted acetic acids (formula I, $R_3$=H, $R_2$=lower alkyl) can also be prepared by a conventional malonate synthesis, starting from the unsubstituted acids (formula I, $R_2$=H, $R_3$=H) in accordance with the following reaction scheme:

The ethyl ester of the α-unsubstituted acid (formula I, $R_2$=H, $R_3$=$C_2H_5$) is treated with ethyl carbonate at elevated temperatures in a basic medium (e.g. sodium ethylate in ethanol) to form the diethyl ester of the corresponding malonic acid of formula (XII), the α-sodium derivative of which is formed by the action of sodium ethylate, and is then alkylated with an alkyl halide to give the α-unsubstituted ethyl malonate of formula (XIII), which is hydrolysed to give the malonic acid of the formula III. The latter is decarboxylated as described above to give the α-substituted acid of formula I ($R_3$=H, $R_2$=alkyl of 1 to 4 carbon atoms).

The invention is illustrated by the following Examples 17–20, 23, 24, 27, 28, 32–34, 36, 37, 39, and 40. The other Examples describe the preparation of starting materials.

EXAMPLE 1

2-Ethyl-1-(thienyl-2′)-propan-3-ol-1-one (Formula V, $R_1$=ethyl)

50 cm³ of a normal solution of potassium hydroxide in ethanol are added dropwise to a solution of 529 g of α-butyrothienone and of 103 g of trioxy-methylene in 250 cm³ of dimethylsulphoxide, at 20° C. The temperature of the reaction mixture rises gradually from 20° to 60° C. and the solution becomes limpid. After the end of the addition, the mixture is stirred for 12 hours whilst allowing it to return to ambient temperature; it is left to stand overnight, water and ice are then added to the reaction mixture, and the whole is extracted with ether. The ether phase is washed 3 times with water and then dried over sodium sulphate. The ether is evaporated in vacuo and the residue obtained (600 g) is fractionally distilled in vacuo. 472 g of 2-ethyl-1-(thienyl-2')-propan-3-ol-1-one b.p. 145°–155° C./3 mm Hg are thus obtained as a colourless liquid.

EXAMPLE 2

2-Isopropyl-1-(thienyl-2')-propan-3-ol-1-one (Formula V, $R_1$ = isopropyl)

Following the procedure of Example 1, but using 569 g of α-isovalerothienone in place of butyrothienone, a precipitate is obtained, after adding water and ice to the reaction mixture, which is filtered off, washed with water and dried, giving 580 g of 2-isopropyl-1-(thienyl-2')-propan-3-ol-1-one in the form of white crystals, m.p. 65°–70° C.

EXAMPLE 3

5-Ethyl-4,5-dihydro-6-oxo-6H-cyclopenta[b]thiophene (Formula VI, $R_1$ = ethyl)

472 g of 2-ethyl-1-(thienyl-2')-propan-3-ol-1-one prepared as in Example 1 are run into 2.4 kg of polyphosphoric acid. The reaction mixture is stirred for 6 hours while the temperature is allowed to rise to 80° C. The reaction mixture is then poured on to ice and the organic products are extracted with ether, carefully washed with water and dried. After evaporation of the solvent, the residue obtained (400 g) is distilled under reduced pressure. This gives 360 g of 5-ethyl-4,5-dihydro-6-oxo-6H-cyclopenta[b]thiophene in the form of a colourless liquid, b.p. 99° C./0.8 mm.Hg.

EXAMPLE 4

5-Isopropyl-4,5-dihydro-6-oxo-6H-cyclopenta[b]thiophene (Formula VI, $R_1$ = isopropyl)

3 kg of polyphosphoric acid are added to 580 g of 2-isopropyl-1-(thienyl-2')-propan-3-ol-1-one, prepared as in Example 2, heated to 70° C. with a waterbath. When the mixture has become homogeneous, the heating is stopped and the temperature of the reaction mixture rises of its own accord to 90° C. When the exothermic effect has subsided, the temperature of the mixture is kept at 80° C. for 6 hours, while stirring. The reaction mixture is then cooled and poured on to ice. The organic products are extracted with ether and the extract is washed carefully with water and dried over sodium sulphate. The organic solvent is evaporated so as to leave a residue of 523 g, which is distilled in vacuo. This gives 480 g of 5-isopropyl-4,5-dihydro-6-oxo-6H-cyclopenta[b]-thiopene in the form of a colourless liquid, b.p. 102°–106° C./0.5 mm Hg.

EXAMPLE 5

5-Ethyl-4,5-dihydro-6H-cyclopenta[b]thiophene (Formula VII, $R_1$ = ethyl)

A mixture of 1.2 kg of zinc powder, 100 g of mercuric chloride, 1 liter of distilled water and 65 cm³ of concentrated hydrochloric acid is stirred for 5 minutes. Stirring is stopped and the mixture is decanted; 1 liter of distilled water and 1 liter of concentrated hydrochloric acid are then added to the alloy with good stirring and the mixture is then brought to the reflux temperature. A solution of 360 g of 5-ethyl-4,5-dihydro-6-oxo-6H-cyclopenta[b]thiophene, prepared as in Example 3, in 750 cm³ of ethanol, is added dropwise to the reaction mixture, with good stirring. The mixture is kept at the reflux temperature for 3 hours. 500 cm³ of concentrated hydrochloric acid are then added in small portions and refluxing is continued for a further three hours, after which a further 500 cm³ of concentrated hydrochloric acid are added in small portions and refluxing is continued for a further 3 hours. The reaction mixture is then cooled and diluted with a mixture of water and ice. The product is extracted with ether. The extract is washed carefully with water and dried over sodium sulphate. The ether is evaporated in vacuo and the residue obtained is subjected to a vacuum distillation. This gives 283 g of 5-ethyl-4,5-dihydro-6H-cyclopenta[b]thiophene as a colourless liquid, b.p. 90°–100° C./10 mm Hg.

EXAMPLE 6

5-Isopropyl-4,5-dihydro-6H-cyclopenta[b]thiophene (Formula VII, $R_1$ = isopropyl)

Following the procedure of Example 5, but using 480 g of 5-isopropyl-4,5-dihydro-6-oxo-6H-cyclopenta[b]-thiophene, prepared as in Example 4, 369 g of 5-isopropyl-4,5-dihydro-6H-cyclopenta[b]thiophene are obtained as a colourless liquid, b.p. 105°–110° C./10 mm.Hg.

EXAMPLE 7

5-Ethyl-4,5-dihydro-6H-cyclopenta[b]thiophene-2-carboxaldehyde (Formula VIII, $R_1$ = ethyl)

115 cm³ of phosphorus oxychloride and 155 cm³ of N-methylformanilide are stirred for 30 minutes at ambient temperature. 228 g of 5-ethyl-4,5-dihydro-6H-cyclopenta[b]thiophene, prepared as in Example 5, are added dropwise to this complex whilst the temperature is maintained at 30° C., if necessary by cooling with iced water. After the end of the addition, the reaction mixture is stirred for a further 6 hours at ambient temperature and is then poured carefully on to a mixture of water and ice. The organic products are extracted with ether. The extract is washed with water until neutral and then dried over sodium sulphate. The ether is evaporated and the residue obtained (290 g) is distilled in vacuo. This gives 205 g of 5-ethyl-4,5-dihydro-6H-cyclopenta[b]thiophene-2-carboxaldehyde as a liquid, b.p. 112°–115° C./0.6 mm Hg.

EXAMPLE 8

5-Isopropyl-4,5-dihydro-6H-cyclopenta[b]thiophene-2-carboxaldehyde (Formula VIII, $R_1$ = isopropyl)

Following the procedure of Example 7, but using 200 g of 5-isopropyl-4,5-dihydro-6H-cyclopenta[b]-thiophene, prepared as in Example 6, 170.5 g of 5-isopropyl-4,5-dihydro-6H-cyclopenta[b]thiophene-2-carboxaldehyde are obtained as crystals of melting point below 50° C., b.p. 130°–135° C./0.5 mm Hg.

EXAMPLE 9

5'-(5-Ethyl-4,5-dihydro-6H-cyclopenta[b]thienylidene-2)-4'-oxo-2'-thioxo-thiazolidine (Formula IX, $R_1$ = ethyl)

A solution of 205 g of 5-ethyl-4,5-dihydro-6H-cyclopenta[b]thiophene-2-carboxaldehyde, prepared as in Example 7, 162 g of rhodanine and 290 g of fused sodium acetate in 900 cm³ of acetic acid is heated at the reflux temperature for 1 hour, while stirring. The reaction mixture is then cooled and poured on to 4 l of distilled water and 2 kg of ice. The crystals formed are carefully filtered off, washed with water and dried. 308 g of 5'-(5-ethyl-4,5-dihydro-6H-cyclopenta[b]thienylidene-2)-4'-oxo-2'-thioxo-thiazolidine are thus obtained as rust-coloured crystals, m.p. 214° C.

EXAMPLE 10

5'-(5-Isopropyl-4,5-dihydro-6H-cyclopenta[b]thienylidene-2)-4'-oxo-2'-thioxo-thiazolidine (Formula IX, $R_1$=isopropyl)

Following the procedure of Example 9, but using 170.5 g of 5-isopropyl-4,5-dihydro-6H-cyclopenta[b]thiophene-2-carboxaldehyde, prepared as in Example 8, 240 g of 5'-(5-isopropyl-4,5-dihydro-6H-cyclopenta[b]thenylidene-2)-4'-oxo-2'-thioxo-thiazolidine are obtained as rust-coloured crystals, m.p. 216°-218° C.

EXAMPLE 11

3'-(5-Ethyl-4,5-dihydro-6H-cyclopenta[b]thienyl-2)-2'-thioxo-propionic acid (Formula X, $R_1$=ethyl)

A solution of 308 g of 5'-(5-ethyl-4,5-dihydro-6H-cyclopenta[b]thienylidene-2)-4'-oxo-2'-thioxo-thiazolidine, prepared as in Example 9, in 1.3 l of 15% sodium hydroxide solution, is heated on a waterbath at 100° C. for 1 hour. The reaction mixture is then cooled to 5° C. and, while it is stirred vigorously, is acidified rapidly to pH 1 with about 2 l of 10% hydrochloric acid. The precipitate formed is filtered off, washed carefully with water and dried. This gives 253 g of 3'-(5-ethyl-4,5-dihydro-6H-cyclopenta[b]thienyl-2)-2'-thioxo-propionic acid as pale yellow crystals, m.p. 205° C.

EXAMPLE 12

3'-(5-Isopropyl-4,5-dihydro-6H-cyclopenta[b]thienyl-2)-2'-thioxo-propionic acid (Formula X, $R_1$=isopropyl)

Following the procedure of Example 11, but using 239.2 g of 5'-(5-isopropyl-4,5-dihydro-6H-cyclopenta[b]thienylidene-2)-4'-oxo-2'-thioxo-thiazolidine, prepared as in Example 10, 205 g of 3'-(5-isopropyl-4,5-dihydro-6H-cyclopenta[b]thienyl-2)-2'-thioxo-propionic acid are obtained as pale yellow crystals, m.p. 195° C.

EXAMPLE 13

3'-(5-Ethyl-4,5-dihydro-6H-cyclopenta[b]thienyl-2)-2'-oximino-propionic acid (Formula XI, $R_1$=ethyl)

A solution of hydroxylamine in ethanol is prepared by adding a solution of 208 g of hydroxylamine hydrochloride in 250 cm³ of water to a solution of sodium ethylate (prepared from 69 g of sodium in 1.5 l of ethanol) and filtering off the sodium chloride formed. This solution of hydroxylamine in ethanol is added to 253 g of 3'-(5-ethyl-4,5-dihydro-6H-cyclopenta[b]thienyl-2)-2'-thioxo-propionic acid, prepared as in Example 11, and the mixture is then heated on a waterbath for 1 hour, during which the solid gradually dissolves and then reprecipitates. The solution is cooled and the precipitate formed is filtered off and dried. This gives 204 g of 3'-(5-ethyl-4,5-dihydro-6H-cyclopenta[b] thienyl-2)-2'-oximino-propionic acid as white crystals m.p. 260° C. (with decomposition).

EXAMPLE 14

3'-(5-Isopropyl-4,5-dihydro-6H-cyclopenta[b]thienyl-2)-2'-oximino-propionic acid (Formula XI, $R_1$=isopropyl)

Following the procedure of Example 13, but using 205 g of 3'-(5-isopropyl-4,5-dihydro-6H-cyclopenta[b]thienyl-2)-2'-thioxo-propionic acid, prepared as in Example 12, 196.5 g of 3'-(5-isopropyl-4,5-dihydro-6H-cyclopenta[b]thienyl-2)-2'-oximino-propionic acid are obtained as slightly yellow crystals, m.p. 215° C. (with decomposition).

EXAMPLE 15

(5-Ethyl-4,5-dihydro-6H-cyclopenta[b]thienyl-2)-acetonitrile (Formula II, $R_1$=ethyl, $R_2$=H)

A solution of 204 g of 3'-(5-ethyl-4,5-dihydro-6H-cyclopenta[b]thienyl-2)-2'-oximino-propionic acid, prepared as in Example 13, in 600 cm³ of acetic anhydride is very gently and carefully heated. When the temperature of the reaction mixture has reached 60° C., a considerable exothermic effect and a vigorous evolution of carbon dioxide gas are observed. After the evolution has ceased and the reaction mixture has returned to ambient temperature, it is heated for 1 hour at 110°-120° C. and then concentrated in vacuo. The residue is taken up in water and extracted with ether. The extract is washed with water, with sodium bicarbonate and again with water. After drying, the ether is evaporated and the residue (190 g) is distilled in vacuo. 119 g of (5-ethyl-4,5-dihydro-6H-cyclopenta[b]thienyl-2)-acetonitrile are thus obtained as a very slightly coloured liquid, b.p. 132° C./0.9 mm Hg.

EXAMPLE 16

(5-Isopropyl-4,5-dihydro-6H-cyclopenta[b]thienyl-2)-acetonitrile (Formula II, $R_1$=isopropyl, $R_2$=H)

Following the procedure of Example 15, but starting from 196.5 g of 3'-(5-isopropyl-4,5-dihydro-6H-cyclopenta[b]thienyl-2)-2'-oximino-propionic acid, prepared as in Example 14, 122.5 g of (5-isopropyl-4,5-dihydro-6H-cyclopenta[b]thienyl-2)-acetonitrile are obtained as pale yellow crystals, m.p. 76°-78° C.

EXAMPLE 17

(5-Ethyl-4,5-dihydro-6H-cyclopenta[b]thienyl-2)-acetic acid (Formula I, $R_1$=ethyl, $R_2$=$R_3$=H)

A solution of 57 g of (5-ethyl-4,5-dihydro-6H-cyclopenta[b]thienyl-2)-acetonitrile, prepared as in Example 15, 50 g of potassium hydroxide in 50 cm³ of water and 500 cm³ of ethanol is heated at the reflux temperature for 7 hours. After it has been cooled, the reaction mixture is poured onto ice and extracted with ether. The aqueous phase is acidified with cold hydrochloric acid and the acid is extracted with ether. The ether phase is washed with water, treated with animal charcoal and dried. After evaporating the ether, 59 g of crystals are obtained, which are recrystallised from petroleum ether. This gives 48 g of (5-ethyl-4,5-dihydro-6H-cyclopent[b]thienyl-2)-acetic acid as white crystals, m.p. 67° C.

EXAMPLE 18

(5-Isopropyl-4,5-dihydro-6H-cyclopenta[b]thienyl-2)-acetic acid (Formula I, $R_1$=isopropyl, $R_2$=$R_3$=H)

Following the procedure of Example 17, but starting from 29.5 g of (5-isopropyl-4,5-dihydro-6H-cyclopenta[b]thienyl-2)-acetonitrile, prepared as in Example 16, 20 g of (5-isopropyl-4,5-dihydro-6H-cyclopenta[b]thienyl-2)-acetic acid are obtained after recrystallisation from petroleum ether, as white crystals, m.p. 118°-119° C.

EXAMPLE 19

The ethyl ester of
(5-ethyl-4,5-dihydro-6H-cyclopenta[b]thienyl-2)-acetic
acid (Formula I, $R_1$=ethyl, $R_2$=H, $R_3$=ethyl)

A solution of 33 g of (5-ethyl-4,5-dihydro-6H-cyclopenta[b]thienyl-2)-acetic acid, prepared as in Example 17, in 100 cm³ of ethanol containing 5 cm³ of concentrated sulphuric acid is heated at the reflux temperature for 5 hours. The reaction mixture is cooled, poured onto a mixture of water and ice and extracted with ether. The ether phase is washed with water until neutral and then dried. The residue is distilled in vacuo, giving 32 g of the ethyl ester of (5-ethyl-4,5-dihydro-6H-cyclopenta[b]thienyl-2)-acetic acid, b.p. 130° C./1.5 mm Hg.

EXAMPLE 20

Ethyl ester of
(5-isopropyl-4,5-dihydro-6H-cyclopenta[b]-thienyl-2)-acetic acid (Formula I, $R_1$=isopropyl, $R_2$=H, $R_3$=ethyl)

Following the procedure of Example 19, but using 12 g of (5-isopropyl-4,5-dihydro-6H-cyclopenta[b]-thienyl-2)-acetic acid, prepared as in Example 18, 11 g of the ethyl ester of this acid are obtained, in the crude state, in the form of crystals of melting point below 40° C.; these are used directly for the subsequent operations, without further purification.

EXAMPLE 21

Diethyl ester of
(5-ethyl-4,5-dihydro-6H-cyclopenta[b]thienyl-2)-malonic acid (Formula XII, $R_1$=ethyl)

A solution of sodium ethylate in ethanol, prepared from 3.9 g of sodium in 100 cm³ of ethanol, is added dropwise to a solution of 32 g of the ethyl ester of (5-ethyl-4,5-dihydro-6H-cyclopenta[b]thienyl-2)-acetic acid in 210 cm³ of diethyl carbonate at 100° C. After the end of the addition, the ethanol, followed by the excess ethyl carbonate, is distilled off until the temperature of the distillation thermometer rises to 125° C. The reaction mixture is cooled, 100 cm³ of water and 20 cm³ of acetic acid are added, and the mixture is then extracted with ether. The extract is washed with water and dried. After evaporation of the ether, 39 g of the crude diethyl ester of (5-ethyl-4,5-dihydro-6H-cyclopenta[b]thienyl-2)-malonic acid are obtained and are used directly for the subsequent operations.

EXAMPLE 22

Diethyl ester of
(5-isopropyl-4,5-dihydro-6H-cyclopenta[b]-thienyl-2)-malonic acid (Formula XII, $R_1$=isopropyl)

Following the procedure of Example 21, but using 11 g of the ethyl ester of (5-isopropyl-4,5-dihydro-6H-cyclopenta[b]thienyl-2)-acetic acid, prepared as in Example 20, 13.5 g of the crude diethyl ester of (5-isopropyl-4,5-dihydro-6H-cyclopenta[b]thienyl-2)-malonic acid are obtained and are used directly for the subsequent operations.

EXAMPLE 23

α-Methyl-(5-ethyl-4,5-dihydro-6H-cyclopenta[b]thienyl-2)-acetic acid (Formula I, $R_1$=ethyl, $R_2$=methyl, $R_3$=H)

39 g of the diethyl ester of (5-ethyl-4,5-dihydro-6H-cyclopenta[b]thienyl-2)-malonic acid, prepared as in Example 21, are added to a solution of sodium ethylate prepared from 3.3 g of sodium in 150 cm³ of ethanol. After the end of the addition, the mixture is stirred for 30 minutes, 25 cm³ of methyl iodide are then added and the whole is heated to the reflux temperature for 2 hours. A further 15 cm³ of methyl iodide are then added and the mixture is heated at the reflux temperature for a further 4 hours. Thereafter, the reaction mixture is concentrated in vacuo and then hydrolysed by heating under reflux for 6 hours in a solution of 125 cm³ of 2.5 N sodium hydroxide solution and 60 cm³ of ethanol. The reaction mixture is then concentrated in vacuo, after which it is taken up in water and the neutral products are extracted with ether. The mother liquors are acidified in the cold with dilute hydrochloric acid and the resulting acid is extracted with ether. After drying, and evaporating the solvent, a residue of 30 g of α-methyl-(5-ethyl-4,5-dihydro-6H-cyclopenta[b]-thienyl-2)-malonic acid is obtained. This acid is decarboxylated by heating in vacuo at 160° C. for 2 hours. The residue obtained is recrystallised from petroleum ether, which gives 17 g of α-methyl-(5-ethyl-4,5-dihydro-6H-cyclopenta[b]thienyl-2)-acetic acid as white crystals, m.p. 75° C.

EXAMPLE 24

α-Methyl-(5-isopropyl-4,5-dihydro-6H-cyclopenta[b]-thienyl-2)-acetic acid (Formula I, $R_1$=isopropyl, $R_2$=methyl, $R_3$=H)

Following the procedure of Example 23, but using 13.5 g of the diethyl ester of (5-isopropyl-4,5-dihydro-6H-cyclopenta[b]thienyl-2)-malonic acid, prepared as in Example 22, 10 g of α-methyl-(5-isopropyl-4,5-dihydro-6H-cyclopenta[b]thienyl-2)-malonic acid are obtained which, after decarboxylation and recrystallisation of the product from heptane, give 6.1 g of α-methyl-(5-isopropyl-4,5-dihydro-6H-cyclopenta[b]thienyl-2)-acetic acid as white crystals, m.p. 115°–116° C.

EXAMPLE 25

α-Methyl-(5-ethyl-4,5-dihydro-6H-cyclopenta[b]thienyl-2)acetonitrile (Formula II, $R_1$=ethyl, $R_2$=CH$_3$)

19.1 g of (5-ethyl-4,5-dihydro-6H-cyclopenta[b]-thienyl-2)-acetonitrile, prepared as in Example 15, in solution in 100 cm³ of benzene, are added to a suspension of 2.5 g of sodium hydride in 50 cm³ of benzene. The mixture is heated at the reflux temperature for 3 hours. Thereafter, the temperature of the reaction mixture is brought to 50° C., 17.5 cm³ of methyl iodide are added and the mixture is then heated at the reflux temperature for 2 hours 30 minutes. The reactants are left in contact overnight at ambient temperature, a further 10 cm³ of methyl iodide are then added and the mixture is heated for a further 4 hours. The reaction mixture is then cooled and water is added. The benzene phase is decanted, washed with water and dried. After evaporation of the solvent, the residue obtained is distilled in vacuo. This gives 9.8 g of α-methyl-(5-ethyl-4,5-dihydro-6H-cyclopenta[b]thienyl-2)-acetonitrile as a liquid, b.p. 130°–150° C./0.5 mm Hg.

EXAMPLE 26

α-Methyl-(5-isopropyl-4,5-dihydro-6H-cyclopenta[b]-thienyl-2)-acetonitrile (Formula II, $R_1$=isopropyl, $R_2$=$CH_3$)

Following the procedure of Example 25, but using 20.5 g of (5-isopropyl-4,5-dihydro-6H-cyclopenta[b]-thienyl-2)-acetonitrile, prepared as in Example 16, 11 g of α-methyl-(5-isopropyl-4,5-dihydro-6H-cyclopenta[b]thienyl-2)-acetonitrile are obtained as white crystals melting below 40° C. and having b.p. 150°–155° C./1 mm Hg.

EXAMPLE 27

α-Methyl-(5-ethyl-4,5-dihydro-6H-cyclopenta[b]thienyl-2)-acetic acid (Formula I, $R_1$=ethyl, $R_2$=$CH_3$, $R_3$=H)

A solution of 9.8 g of α-methyl-(5-ethyl-4,5-dihydro-6H-cyclopenta[b]thienyl-2)-acetonitrile, prepared as in Example 25, in 100 cm³ of 80% ethanol containing 9 g of potassium hydroxide is heated under reflux for 8 hours. The reaction mixture is then cooled, after which it is treated with ice and water. The neutral products are extracted with ether. The mother liquors are acidified in the cold with hydrochloric acid, the resulting acid is then extracted with ether, and the extract is washed with water and dried. After evaporating the ether, and recrystallising the crystals obtained from petroleum ether, 6 g of α-methyl-(5-methyl-4,5-dihydro-6H-cyclopenta[b]thienyl-2)-acetic acid are obtained as white crystals, m.p. 75° C.

EXAMPLE 28

α-Methyl-(5-isopropyl-4,5-dihydro-6H-cyclopenta[b]-thienyl-2)-acetic acid (Formula I, $R_1$=isopropyl, $R_2$=$CH_3$, $R_3$=H)

Following the procedure of Example 27, but using 11 g of α-methyl-(5-isopropyl-4,5-dihydro-6H-cyclopenta[b]-thienyl-2)-acetonitrile, prepared as in Example 26, 6.3 g of α-methyl-(5-isopropyl-4,5-dihydro-6H-cyclopenta[b]thienyl-2)-acetic acid are obtained after recrystallisation from heptane as white crystals, m.p. 115°–116° C.

EXAMPLE 29

α-Methyl-(5-ethyl-4,5-dihydro-6H-cyclopenta[b]thienyl-2)-acetyl chloride (Formula IV, $R_1$=ethyl, $R_2$=methyl)

A solution of 8 g of α-methyl-(5-ethyl-4,5-dihydro-6H-cyclopenta[b]thienyl-2)-acetic acid, prepared as in Example 23, and of 3.1 cm³ of thionyl chloride in 50 cm³ of benzene is heated under reflux for 2 hours. The reaction mixture is then concentrated in vacuo and the crude acid chloride obtained (8.4 g) is used directly for the following stages.

EXAMPLE 30

Hydrochloride of the morpholinoethyl ester of α-methyl(5-ethyl-4,5-dihydro-6H-cyclopenta[b]thienyl-2)-acetic acid

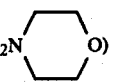
(Formula I, $R_1$ = ethyl, $R_2$ = $CH_3$, $R_3$ = $CH_2CH_2N$⟨O⟩)

A solution of 8.4 g of the chloride of α-methyl(5-ethyl-4,5-dihydro-6H-cyclopenta[b]thienyl-2)-acetic acid, prepared as in Example 29, in 50 cm³ of benzene is added dropwise to a solution of 5.1 g of β-morpholinoethanol and 6 cm³ of triethylamine in 50 cm³ of benzene. When the exothermic effect has subsided, the mixture is heated to 60° C. on a water-bath for 3 hours and then cooled and poured into 100 cm³ of water. The benzene layer is decanted, washed carefully with water, passed through active charcoal and then dried. After evaporation of the benzene, the residue obtained is taken up in ether and a solution of hydrogen chloride in ether is added until the pH is neutral. The precipitate obtained is washed carefully with ether and recrystallised from isopropanol. This gives 10.7 g of the hydrochloride of the β-morpholinoethyl ester of α-methyl-(5-ethyl-4,5-dihydro-6H-cyclopenta[b]thienyl-2)-acetic acid as beige crystals, m.p. 151° C.

EXAMPLE 31

(5-Ethyl-4,5-dihydro-6H-cyclopenta[b]thienyl-2)-acetyl chloride (Formula IV, $R_1$=ethyl, $R_2$=H)

Following the procedure of Example 29, but using 25 g of (5-ethyl-4,5-dihydro-6H-cyclopenta[b]thienyl-2)-acetic acid, 28 g of the above acid chloride are obtained, and are used in the crude state for the subsequent operations.

EXAMPLE 32

Hydrochloride of the morpholinoethyl ester of (5-ethyl-4,5-dihydro-6H-cyclopenta[b]thienyl-2)-acetic acid

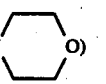
(Formula I, $R_1$ = ethyl, $R_2$ = H, $R_3$ = $CH_2CH_2N$⟨O⟩)

Following the procedure of Example 30, but using 12.6 g (5-ethyl-4,5-dihydro-6H-cyclopenta[b]thienyl-2)-acetyl chloride, 9.5 g of the hydrochloride of the morpholinoethyl ester of (5-ethyl-4,5-dihydro-6H-cyclopenta[b]thienyl-2)-acetic acid are obtained after recrystallisation from isopropanol, as beige crystals, m.p. 155° C.

EXAMPLE 33

Hydrochloride of the dimethylaminoethyl ester of (5-ethyl-4,5-dihydro-6H-cyclopenta[b]thienyl-2)-acetic acid

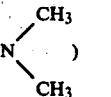
(Formula I, $R_1$ = ethyl, $R_2$ = H, $R_3$ = $CH_2CH_2N(CH_3)_2$)

Following the procedure of Example 30, but using 12.6 g of (5-ethyl-4,5-dihydro-6H-cyclopenta[b]thienyl- 2)-acetyl chloride and 5.4 g of dimethylaminoethanol, 10.8 g of the hydrochloride of the dimethylaminoethyl ester of (5-ethyl-4,5-dihydro-6H-cyclopenta[b]thienyl-2)-acetic acid are obtained as beige crystals, m.p. 172° C.

EXAMPLE 34

Hydrochloride of the dimethylaminoethyl ester of α-methyl-(5-ethyl-4,5-dihydro-6H-cyclopenta[b]thienyl-2)-acetic acid

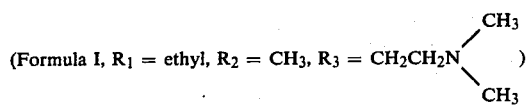

Following the procedure of Example 30, but using 11.6 g of α-methyl-(5-ethyl-4,5-dihydro-6H-cyclopenta[b]-thienyl-2)-acetyl chloride prepared as in Example 29 and 4.7 g of dimethylaminoethanol, 10.4 g of the hydrochloride of the dimethylaminoethyl ester of α-methyl-(5-ethyl-4,5-dihydro-6H-cyclopenta[b]thienyl-2)-acetic acid are obtained after recrystallisation from isopropanol as white crystals m.p. 122°–124° C.

EXAMPLE 35

α-Methyl-(5-isopropyl-4,5-dihydro-6H-cyclopenta[b]-thienyl-2)-acetyl chloride (Formula IV, $R_1$=isopropyl, $R_2$=methyl)

Following the procedure of Example 29, but using 20 g of α-methyl-(5-isopropyl-4,5-dihydro-6H-cyclopenta[b]-thienyl-2)-acetic acid prepared as in Example 28, 20.9 g of this acid chloride are obtained, and are used in the crude state for the following operations.

EXAMPLE 36

Hydrochloride of the morpholinoethyl ester of α-methyl-(5-isopropyl-4,5-dihydro-6H-cyclopenta[b]-thienyl-2)-acetic acid

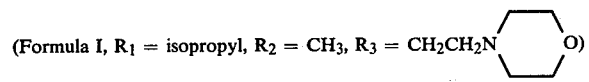

Following the procedure of Example 30, but using 9.4 g of α-methyl-(5-isopropyl-4,5-dihydro-6H-cyclopenta[b]-thienyl-2)-acetyl chloride prepared as in Example 35 and 5.3 g of β-morpholinoethanol, 7 g of the hydrochloride of the β-morpholinoethyl ester of α-methyl-(5-isopropyl-4,5-dihydro-6H-cyclopenta[b]-thienyl-2)-acetic acid, are obtained after recrystallisation from isopropanol as white crystals, m.p. 153°–155° C.

EXAMPLE 37

Hydrochloride of the dimethylaminoethyl ester of α-methyl-(5-isopropyl-4,5-dihydro-6H-(cyclopenta[b]-thienyl-2)-acetic acid

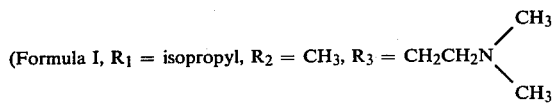

Following the procedure of Example 30, but using 9.4 g of α-methyl-(5-isopropyl-4,5-dihydro-6H-cyclopenta[b]-thienyl-2)-acetyl chloride prepared as in Example 35 and 3.6 g of β-dimethylaminoethanol, 7.6 g of the hydrochloride of the β-dimethylaminoethyl ester of α-methyl-(5-isopropyl-4,5-dihydro-6H-cyclopenta[b]thienyl-2)-acetic acid are obtained after recrystallisation from isopropanol as white crystals, m.p. 136°–138° C.

EXAMPLE 38

(5-Isopropyl-4,5-dihydro-6H-cyclopenta[b]thienyl-2)-acetyl chloride (Formula IV, $R_1$=isopropyl, $R_2$=H)

Following the same procedure as in Example 29, but using 22.2 g of (5-isopropyl-4,5-dihydro-6H-cyclopenta[b]thienyl-2)-acetic acid, prepared as in Example 18, 23 g of this acid chloride are obtained and are used in the crude state for the following operations.

EXAMPLE 39

Hydrochloride of the morpholinoethyl ester of (5-isopropyl-4,5-dihydro-6H-cyclopenta[b]thienyl-2)-acetic acid

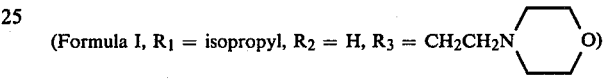

Following the procedure of Example 30, but using 10.2 g of (5-isopropyl-4,5-dihydro-6H-cyclopenta[b]-thienyl-2)-acetyl chloride prepared as in Example 38 and 6 g of β-morpholinoethanol, 7.6 g of the hydrochloride of the β-morpholinoethyl ester of (5-isopropyl-4,5-dihydro-6H-cyclopenta[b]thienyl-2)-acetic acid are obtained after recrystallisation from isopropanol, as beige crystals, m.p. 179°–181° C.

EXAMPLE 40

Hydrochloride of the dimethylaminoethyl ester of (5-isopropyl-4,5-dihydro-6H-cyclopenta[b]thienyl-2)-acetic acid

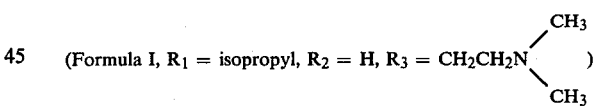

Following the procedure of Example 30, but using 10.2 g of (5-isopropyl-4,5-dihydro-6H-cyclopenta[b]-thienyl-2)-acetyl chloride, prepared as in Example 38, and 4.1 g of β-dimethylaminoethanol, 6.4 g of the hydrochloride of the β-dimethylaminoethyl ester of (5-isopropyl-4,5-dihydro-6H-cyclopenta[b]thienyl-2)-acetic acid are obtained after recrystallisation from isopropanol as beige crystals, m.p. 189°–192° C.

The pharmacological properties of the cyclopenta[b]-thiophene derivatives of formula I are illustrated below.

I. Anti-inflammatory activity (A) Method

Batches of 12 male SPF rats, strain OFA, weighing 120–130 g each, are given the product to be tested by oral administration 2 hours before and 30 minutes before (½ dose each time) subcutaneous plantar injection of 0.05 cm³ of a 1% solution of carrageenin. The volume of the rear paw which has received the carrageenin is measured at regular intervals.

B) Results

| mg/kg oral administration | Example 17 | Example 18 | Examples 23 & 27 | Examples 24 & 28 | Example 30 | Example 32 | Example 33 | Example 34 | Example 36 | Example 37 | Example 39 | Example 40 |
|---|---|---|---|---|---|---|---|---|---|---|---|---|
| 4 | 17 | 0 | | 0 | 18 | 0 | 2 | 3 | 29 | 5 | 7 | 8 |
| 16 | 24 | 0 | 30 | 32 | 38 | 16 | 17 | 12 | 30 | 35 | 23 | 7 |
| 64 | 55 | 31 | 67 | 63 | 53 | 20 | 55 | 45 | 62 | 45Z | 20 | 13 |
| 128 | 52 47 | 66 | 59 | 67 | 51 | 54 | 64 | 56 | 63 | 53 | 22 | |
| 256 | 66 | 57 | 56 | 46 | 79 | 53 | 52 | 82 | 66 | 58 | 56 | 32 |

II. Analgesic activity

(A) Method

Batches of 6 male mice ($SPF_1$, strain $OF_1$), weighing 19–20 g each are given the product to be tested, by oral administration. One hour afterwards, each mouse is injected intraperitoneally with 0.3 cm³ of an 0.02% strength phenylbenzoquinone solution and from the 5th to the 10th minute after this latter treatment, the number of pain reactions (abdominal contortions) is counted. The table which follows gives the percentage inhibition of these reactions.

B) Results

| mg/kg oral administration | Example 17 | Example 18 | Examples 23 & 27 | Examples 24 & 28 | Example 30 | Example 32 | Example 33 | Example 34 | Example 36 | Example 37 | Example 39 | Example 40 |
|---|---|---|---|---|---|---|---|---|---|---|---|---|
| 4 | — | — | — | 0 | — | — | — | 21 | — | 10 | — | — |
| 8 | — | — | 7 | 35 | 9 | — | — | 46 | 23 | 53 | — | — |
| 16 | 17 | 4 | 35 | 66 | 6 | 25 | 37 | 74 | 80 | 42 | — | 0 |
| 32 | 58 | 27 | 79 | 89 | 85 | 48 | — | 95 | 84 | 80 | — | — |
| 64 | 63 | 61 | 98 | 96 | 93 | 53 | 17 | — | — | — | 12 | 31 |
| 256 | — | — | — | — | — | — | 95 | — | — | — | 53 | 88 |

The compound of formula I exhibits anti-inflammatory, anti-rheumatic and analgesic pharmacological properties. They can be used in therapy in the form of pills containing 200 mg each, of suppositories containing 500 mg each, of injectable solutions containing 100 mg per 2 cm³ of solvent, or of ointments containing 3% of active principle, in the therapy of inflammations of any origin, in particular rheumatic inflammations, and in the prevention and therapy of pain. The most interesting compounds are the acids of Examples 23 and 24 and their esters of Examples 30, 34, 36, and 37.

I claim:

1. Cyclopenta[b]thiophene derivatives of the formula:

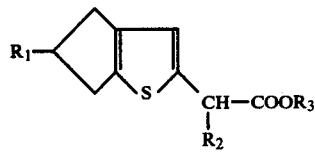

in which $R_1$ represents straight-chain or branched-chain alkyl of 1 to 4 carbon atoms, $R_2$ represents hydrogen or alkyl of 1 to 4 carbon atoms, and $R_3$ represents aminoalkyl of the formula:

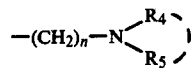

where n is 2 or 3 and $R_4$ and $R_5$ taken together form, with the nitrogen atom to which they are attached, the morpholino group, and the non-toxic, pharmaceutically acceptable inorganic salts and acid addition salts of the said derivatives.

2. Cyclopenta[b]thiophene derivatives as claimed in claim 1, in which $R_1$ is ethyl or isopropyl, $R_2$ is hydrogen or methyl, and $R_3$ is morpholinoethyl, and the non-toxic pharmaceutically acceptable inorganic salts of said derivatives.

3. A derivative as claimed in claim 1 which is the morpholinoethyl ester of α-methyl-5-isopropyl-4,5-dihydro-6H-cyclopenta[b]thiophene-2-acetic acid or a non-toxic pharmaceutically acceptable acid addition salt thereof.

4. A derivative as claimed in claim 1 which is the morpholinoethyl ester of α-methyl-5-isopropyl-4,5-dihydro-6H-cyclopenta[b]thiophene-2-acetic acid or a non-toxic pharmaceutically acceptable acid addition salt thereof.

5. A derivative as claimed in claim 1 which is the morpholinoethyl ester of 5-ethyl-4,5-dihydro-6H-cyclopenta[b]thiophene-2-acetic acid or a non-toxic pharmaceutically acceptable acid addition salt thereof.

6. A pharmaceutical composition comprising an analgesic or anti-inflammatory effective amount of a cyclopenta[b]thiophene derivative or a non-toxic pharmaceutically acceptable salt thereof as claimed in claim 1 and a non-toxic, pharmaceutically acceptable carrier.

7. A composition according to claim 6, in the form of pills containing 200 mg of active ingredient each or suppositories containing 500 mg of active ingredient each or an injectable solution containing 100 mg of active ingredient per 2 cm³ or an ointment containing 3% of active ingredient.

8. Pharmaceutical composition according to claim 6, in which the active ingredient is the morpholino-ethyl ester of α-methyl-5-isopropyl-4,5-dihydro-6H-cyclopenta[b]thiophene-2-acetic acid or an addition salt of this ester with a non-toxic acid.

9. Pharmaceutical composition according to claim 6, in which the active ingredient is the morpholino-ethyl ester of α-methyl-5-ethyl-4,5-dihydro-6H-cyclopenta[b]thiophene-2-acetic acid, or an addition salt of this ester with a non-toxic acid.

* * * * *